United States Patent
Metcalf

(10) Patent No.: US 12,419,855 B2
(45) Date of Patent: Sep. 23, 2025

(54) COMPOSITIONS COMPRISING CANNABINOID IONS THAT ARE DISSOLVED IN GLYCEROL

(71) Applicant: Natural Extraction Systems, LLC, Boulder, CO (US)

(72) Inventor: Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 883 days.

(21) Appl. No.: 17/638,701

(22) PCT Filed: Aug. 27, 2020

(86) PCT No.: PCT/US2020/048152
§ 371 (c)(1),
(2) Date: Feb. 25, 2022

(87) PCT Pub. No.: WO2021/041637
PCT Pub. Date: Mar. 4, 2021

(65) Prior Publication Data
US 2023/0000817 A1    Jan. 5, 2023

Related U.S. Application Data

(60) Provisional application No. 62/971,795, filed on Feb. 7, 2020, provisional application No. 62/950,811, filed on Dec. 19, 2019, provisional application No. 62/935,487, filed on Nov. 14, 2019, provisional application No. 62/928,949, filed on Oct. 31, 2019, provisional application No. 62/923,410, filed on Oct. 18, 2019, provisional application No. 62/892,925, filed on Aug. 28, 2019.

(51) Int. Cl.
*A61K 31/352* (2006.01)
*A61K 9/00* (2006.01)
*A61K 47/10* (2017.01)
*C07D 311/80* (2006.01)

(52) U.S. Cl.
CPC .......... *A61K 31/352* (2013.01); *A61K 9/0014* (2013.01); *A61K 9/0053* (2013.01); *A61K 47/10* (2013.01); *C07D 311/80* (2013.01)

(58) Field of Classification Search
CPC ...... A61K 31/05; A61K 31/352; A61K 47/10; A61K 9/0095; A61K 36/185; A61K 47/02; A61K 9/0053; A61K 9/08; A61K 31/055; A61K 31/00; A61K 2300/00; A61K 31/047; A61K 31/235; A61K 31/01; A61K 31/015; A61K 31/045; A61K 31/19; A61K 31/192; A61K 31/198; A61K 31/20; A61K 31/355; A61K 31/401; A61K 31/405; A61K 31/4172; A61K 36/07; A61K 36/074; A61K 36/23; A61K 36/282; A61K 36/324; A61K 36/48; A61K 36/71; A61K 36/889; A61K 36/9066; A61K 47/14; A61K 47/22; A61K 47/26; A61K 47/44; A61K 9/008; A61K 31/658; A61K 45/06; A61K 9/0073; A61K 9/12; A61K 9/1617; A61K 9/1623; A61P 25/08; A61P 1/08; A61P 25/18; A61P 21/02; A61P 23/00; A61P 25/06; A61P 27/06; A61P 29/00; A61P 35/00; A61P 37/02; A61P 9/12; A61P 25/00; A61P 25/04; A61P 25/22; A61P 25/36; A61P 39/00; A61P 19/02; A61P 25/16; A61P 25/28; A61P 25/30; A61P 25/34; A61P 3/00; A61P 3/04; A61P 43/00

See application file for complete search history.

(56) References Cited

FOREIGN PATENT DOCUMENTS

| EP | 3351242 A1 | 7/2018 | |
|---|---|---|---|
| WO | WO2017/216362 A1 * | 12/2017 | ........... C07D 311/80 |
| WO | 2019036243 A1 | 2/2019 | |

* cited by examiner

*Primary Examiner* — Audrea B Coniglio
(74) *Attorney, Agent, or Firm* — Douglas G. Metcalf

(57) ABSTRACT

Various aspects of this patent document relate to cannabinoid ions that are dissolved in glycerol, in which the cannabinoid ions are not carboxylates.

20 Claims, No Drawings

COMPOSITIONS COMPRISING CANNABINOID IONS THAT ARE DISSOLVED IN GLYCEROL

CROSS-REFERENCE TO RELATED APPLICATIONS

This patent document is the U.S. national stage under 35 U.S.C. § 371 of international application PCT/US20/48152, filed Aug. 27, 2020, which claims priority to U.S. Provisional Patent Application No. 62/892,925, filed Aug. 28, 2019; U.S. Provisional Patent Application No. 62/923,410, filed Oct. 18, 2019; U.S. Provisional Patent Application No. 62/928,949, filed Oct. 31, 2019; U.S. Provisional Patent Application No. 62/935,487, filed Nov. 14, 2019; U.S. Provisional Patent Application No. 62/950,811, filed Dec. 19, 2019; and U.S. Provisional Patent Application No. 62/971,795, filed Feb. 7, 2020, each of which is incorporated by reference in its entirety.

BACKGROUND

Cannabinoids consumed through conventional routes such as by inhalation or oral ingestion are oxidized by cytochrome P450 in the lungs and liver, respectively. Cannabinoid formulations that minimize or avoid cytochrome P450 mediated oxidation are desirable.

SUMMARY

Various aspects of this patent document relate to cannabinoid ions that are dissolved in glycerol and that convert into cannabinoid molecules at neutral pH. The cannabinoid ions are anions that carry net negative charges that repel each other to maximize their surface area. The cannabinoid ions are not carboxylates because carboxylates generally do not convert to molecules at neutral pH.

The administration of cannabinoid ions that are dissolved in glycerol to a human or an animal results in the pH-dependent conversion of the cannabinoid ions into cannabinoid molecules, which are generally insoluble in both glycerol and bodily fluids. The cannabinoid molecules then rapidly partition out of the glycerol and adhere to the epithelium where they absorb into the blood (during oral administration) or the skin and underlying tissue (during topical administration). Absorption through the epithelium of the mouth and throat avoids first-pass metabolism, which minimizes cytochrome P450 mediated oxidation and improves pharmacokinetics.

DETAILED DESCRIPTION

Various aspects of this patent document relate to a composition, comprising a liquid phase that comprises a solute and a solvent, wherein the solute is a cannabinoid ion; the cannabinoid ion is an anion that has a net charge of −1; the cannabinoid ion lacks a carboxylate group; the solvent is glycerol; and the cannabinoid ion is dissolved in the glycerol. "Comprising" and "comprise(s)" refer to open-ended sets such that a liquid phase that comprises a solute and a solvent can also comprise, for example, a metal cation. "Carboxylate group" refers to $-(C=O)O^-$. "Glycerol" is synonymous with glycerin, glycerine, and propane-1,2,3-triol. "Dissolved" refers to a solute that is solvated in a liquid phase by either (i) a solvent, (ii) a cosolvent, or (iii) both a solvent and a cosolvent; a chemical species that is present within a phase that is dispersed within a liquid phase, such as the dispersed phase of an emulsion, is not dissolved in the liquid phase; a chemical species that is non-covalently bound to any chemical species that is a solid in the absence of a solvent, such as a cyclodextrin, is not dissolved in a solvent.

U.S. Pat. No. 10,555,914 B1 discloses "methods of producing anionic cannabinoid molecules dissolved in water." These methods are generally applicable to produce compositions comprising a cannabinoid ion that is dissolved in glycerol, for example, by substituting glycerol for the water of the methods of U.S. Pat. No. 10,555,914. Any known cannabinoid can be converted into a cannabinoid ion according to the methods of U.S. Pat. No. 10,555,914. Additional cannabinoid ions are disclosed in PCT Patent Application Publication No. WO 2020/123809 A1. The scope of the term "anionic cannabinoid molecule" as used in U.S. Pat. No. 10,555,914 and WO 2020/123809 encompasses the term "cannabinoid ion" as used in this patent document. This patent document incorporates each of U.S. Pat. No. 10,555,914 and WO 2020/123809 by reference in its entirety to delineate specific and generic anionic cannabinoid molecules that fall within the scope of "cannabinoid ion" as the term is used in the specification and claims of this patent document.

In some embodiments, the composition comprises the glycerol at a concentration of at least 50 percent by weight. In some specific embodiments, the composition comprises the glycerol at a concentration of at least 65 percent by weight. In some very specific embodiments, the composition comprises the glycerol at a concentration of at least 65 percent and no greater than 90 percent by weight.

In some embodiments, the composition comprises ethanol. In some specific embodiments, the composition comprises ethanol at a concentration of at least 1 percent and no greater than 12 percent by weight. In some specific embodiments, the composition comprises ethanol at a concentration of at least 9 percent and no greater than 29 percent by weight. In some specific embodiments, the composition comprises ethanol at a concentration of at least 20 percent and no greater than 49 percent by weight.

In some embodiments, the composition comprises water. In some specific embodiments, the composition comprises water at a concentration of at least 0.1 percent and no greater than 20 percent by weight. In some very specific embodiments, the composition comprises water at a concentration of at least 0.1 percent and no greater than 10 percent by weight.

In some embodiments, the composition comprises a metal cation. In some specific embodiments, the composition comprises the metal cation and the cannabinoid ion at a molar ratio of at least 1:1 and no greater than 5:4. In some specific embodiments, the metal cation is sodium cation ("Na+"). In some very specific embodiments, the composition comprises sodium ion at a concentration of at least 10 parts per million and no greater than 1 percent by weight. In some specific embodiments, the metal cation is potassium cation ("K+"). In some very specific embodiments, the composition comprises potassium ion at a concentration of at least 10 parts per million and no greater than 1 percent by weight.

In some embodiments, the composition comprises a concentration of the cannabinoid ion that is dissolved in the glycerol, wherein the cannabinoid ion has a conjugate acid; the conjugate acid has a solubility in the liquid phase; and the solubility of the conjugate acid in the liquid phase is less than the concentration of the cannabinoid ion that is dissolved in the glycerol. In some specific embodiments, the concentration of the cannabinoid ion that is dissolved in the glycerol is at least double the solubility of the conjugate acid in the liquid phase. "Solubility" refers to the ability of a chemical species (for example, molecular cannabidiol, which is the conjugate acid of the cannabidiol anion) to dissolve in a solvent as the same chemical species (molecular cannabidiol) and does not refer to the ability of a chemical species (for example, molecular cannabidiol) to dissolve in a solvent as a different chemical species (for example, as the cannabidiol anion); the empirical measurement of "solubility" may require—but does not necessarily require—a composition or liquid phase that has a lower pH than the compositions and liquid phases disclosed and claimed in this patent document, but that is otherwise identical to the compositions and liquid phases disclosed and claimed in this patent document.

In some embodiments, the composition comprises a concentration of the cannabinoid ion that is dissolved in the glycerol, wherein the cannabinoid ion has a conjugate acid; the conjugate acid has a solubility in water; and the solubility of the conjugate acid in water is less than the concentration of the cannabinoid ion that is dissolved in the glycerol. In some specific embodiments, the concentration of the cannabinoid ion that is dissolved in the glycerol is at least 10 times greater than the solubility of the conjugate acid in water. In some specific embodiments, the concentration of the cannabinoid ion that is dissolved in the glycerol is at least 100 times greater than the solubility of the conjugate acid in water.

In some embodiments, the composition comprises a molecule and the cannabinoid ion at a molar ratio of at least 1:1,000,000 and no greater than 10:1, wherein the cannabinoid ion has a conjugate acid; and the molecule is the conjugate acid of the cannabinoid ion. In some specific embodiments, the composition comprises the molecule and the cannabinoid ion at a molar ratio of at least 1:1,000,000 and less than 1:1. In some very specific embodiments, the composition comprises the molecule and the cannabinoid ion at a molar ratio of at least 1:1000 and no greater than 9:10.

In some embodiments, the composition comprises the cannabinoid ion at a concentration of at least 0.1 grams per liter. In some specific embodiments, the composition comprises the cannabinoid ion at a concentration of at least 1 gram per liter. In some specific embodiments, the composition comprises the cannabinoid ion at a concentration of at least 1 gram per liter and no greater than 100 grams per liter. In some very specific embodiments, the composition comprises the cannabinoid ion at a concentration of at least 10 grams per liter and no greater than 100 grams per liter.

In some embodiments, the cannabinoid ion comprises an aromatic ring and an oxide group (—O$^-$); the oxide group is a substituent on the aromatic ring; and the cannabinoid ion is an anion because the oxide group has a net charge of −1. Each of the generic and specific cannabinoid ions disclosed in this patent document comprise an aromatic ring and an oxide group (—O$^-$), in which both (i) the oxide group is a substituent on the aromatic ring, and (ii) the cannabinoid ion is an anion because the oxide group has a net charge of −1

In some embodiments, the cannabinoid ion has the general formula I, II, III, IV, V, VI, VII, or VIII, which are set forth below.

In some embodiments, $R_1$ is selected from H; a straight or branched $C_1$-$C_{12}$ alkyl that is optionally substituted by at least one of hydroxy, a halogen, phenyl, and a cycloalkyl; and a straight or branched $C_2$-$C_{12}$ alkenyl that is optionally substituted by at least one of hydroxy, a halogen, phenyl, and a cycloalkyl. "Straight or branched $C_1$-$C_{12}$ alkyl" refers to a straight or branched hydrocarbon chain having 1, 2, 3, 4, 5, 6, 7, 8, 9, 10, 11, or 12 carbon atoms, wherein all carbon-carbon bonds in the hydrocarbon chain are single bonds. "Substituted by at least one of hydroxy, a halogen, phenyl, and a cycloalkyl" refers to the substitution of at least one hydrogen atom of a hydrocarbon chain with either hydroxy, a halogen, phenyl, or a cycloalkyl. "Halogen" refers to F, Cl, Br, and I. "Cycloalkyl" refers to cyclopropyl, cyclobutyl, cyclopentyl, cyclohexyl, cycloheptyl, and adamantyl. When a hydrocarbon chain is substituted by a cycloalkyl, then either (i) a single hydrogen atom of the hydrocarbon chain is substituted with the cycloalkyl such that the cycloalkyl does not include any carbon atom of the hydrocarbon chain, or (ii) two hydrogen atoms of the

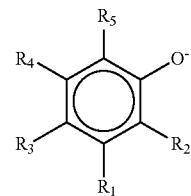

I

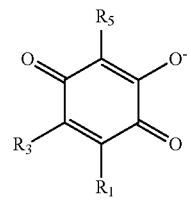

II

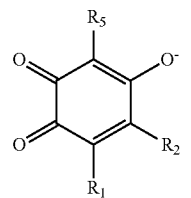

III

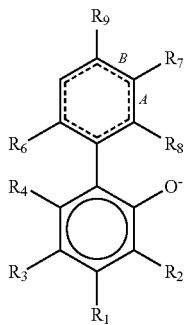

IV

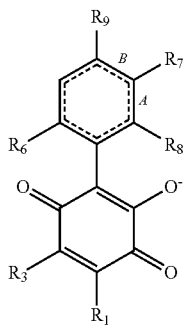

V

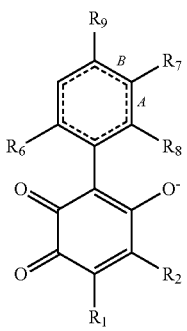

VI

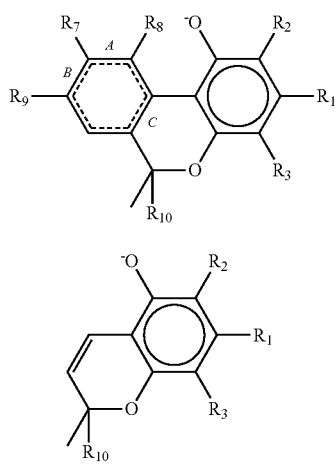

VII

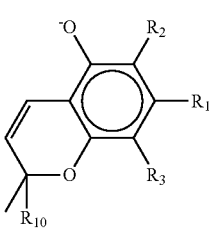

VIII hydrocarbon chain are substituted with the cycloalkyl such that the cycloalkyl comprises one or more carbon atoms of the hydrocarbon chain. "Straight or branched $C_2$-$C_{12}$ alkenyl" refers to a straight or branched hydrocarbon chain having 2, 3, 4, 5, 6, 7, 8, 9, 10, 11, or 12 carbon atoms, wherein at least one carbon-carbon bond in the hydrocarbon chain is a double bond and no carbon-carbon bond in the hydrocarbon chain is a triple bond.

In some embodiments, $R_2$, $R_3$, $R_8$, and $R_9$ are each independently selected from H and a halogen. In some specific embodiments, each of $R_2$, $R_3$, $R_8$, and $R_9$ are H. In some specific embodiments, $R_2$ is F; and each of $R_3$, $R_8$, and $R_9$ are H. In some specific embodiments, $R_3$ is F; and each of $R_2$, $R_8$, and $R_9$ are H. In some specific embodiments, $R_8$ is F; and each of $R_2$, $R_3$, and $R_9$ are H. In some specific embodiments, $R_9$ is F; and each of $R_2$, $R_3$, and $R_8$ are H.

In some embodiments, $R_4$ is selected from H, hydroxy, methoxy, ethoxy, 2-propoxy, and —OC(=O)$R_{11}$.

In some embodiments, $R_5$ is selected from a straight or branched $C_5$-$C_{12}$ alkyl that is optionally substituted by at least one of hydroxy, a halogen, phenyl, and a cycloalkyl; a straight or branched $C_5$-$C_{12}$ alkenyl that is optionally substituted by at least one of hydroxy, a halogen, phenyl, and a cycloalkyl; and a straight or branched $C_5$-$C_{12}$ alkynyl that is optionally substituted by at least one of hydroxy, a halogen, phenyl, and a cycloalkyl. "Straight or branched $C_5$-$C_{12}$ alkyl" refers to a straight or branched hydrocarbon chain having 5, 6, 7, 8, 9, 10, 11, or 12 carbon atoms, wherein all carbon-carbon bonds in the hydrocarbon chain are single bonds. "Straight or branched $C_5$-$C_{12}$ alkenyl" refers to a straight or branched hydrocarbon chain having 5, 6, 7, 8, 9, 10, 11, or 12 carbon atoms, wherein at least one carbon-carbon bond in the hydrocarbon chain is a double bond and no carbon-carbon bond in the hydrocarbon chain is a triple bond. "Straight or branched $C_5$-$C_{12}$ alkynyl" refers to a straight or branched hydrocarbon chain having 5, 6, 7, 8, 9, 10, 11, or 12 carbon atoms, wherein at least one carbon-carbon bond in the hydrocarbon chain is a triple bond.

In some embodiments, $R_6$ is selected from H; a halogen; a straight of branched $C_1$-$C_6$ alkyl that is optionally substituted by at least one of hydroxy and a halogen; a straight of branched $C_2$-$C_6$ alkenyl that is optionally substituted by at least one of hydroxy and a halogen; and a straight of branched $C_2$-$C_6$ alkynyl that is optionally substituted by at least one of hydroxy and a halogen. "Straight or branched $C_1$-$C_6$ alkyl" refers to a straight or branched hydrocarbon chain having 1, 2, 3, 4, 5, or 6 carbon atoms, wherein all carbon-carbon bonds in the hydrocarbon chain are single bonds. "Straight or branched $C_2$-$C_6$ alkenyl" refers to a straight or branched hydrocarbon chain having 2, 3, 4, 5, or 6 carbon atoms, wherein at least one carbon-carbon bond in the hydrocarbon chain is a double bond and no carbon-carbon bond in the hydrocarbon chain is a triple bond. "Straight or branched $C_2$-$C_6$ alkynyl" refers to a straight or branched hydrocarbon chain having 2, 3, 4, 5, or 6 carbon atoms, wherein at least one carbon-carbon bond in the hydrocarbon chain is a triple bond. "Substituted by at least one of hydroxy and a halogen" refers to the substitution of at least one hydrogen atom of a hydrocarbon chain with either hydroxy or a halogen.

In some embodiments, $R_7$ is selected from H; a halogen; hydroxy; oxo; methylidene; a straight or branched $C_1$-$C_6$ alkyl that is optionally substituted by at least one of hydroxy and a halogen; a straight or branched $C_2$-$C_6$ alkenyl that is optionally substituted by at least one of hydroxy and a halogen; a straight or branched $C_2$-$C_6$ alkynyl that is optionally substituted by at least one of hydroxy and a halogen; and —C(=O)$R_{12}$.

In some embodiments, $R_{10}$ is selected from H; a halogen; hydroxy; a straight of branched $C_1$-$C_6$ alkyl that is optionally substituted by at least one of hydroxy and a halogen; a straight of branched $C_2$-$C_6$ alkenyl that is optionally substituted by at least one of hydroxy and a halogen; and a straight of branched $C_2$-$C_6$ alkynyl that is optionally substituted by at least one of hydroxy and a halogen.

In some embodiments, $R_{11}$ is selected from a straight or branched $C_1$-$C_6$ alkyl.

In some embodiments, $R_{12}$ is selected from H; a straight or branched $C_1$-$C_6$ alkyl; and a straight or branched $C_1$-$C_6$ alkoxy. "Straight or branched $C_1$-$C_6$ alkoxy" refers to —O$R_{13}$, wherein $R_{13}$ is a straight or branched $C_1$-$C_6$ alkyl.

In some embodiments, the dotted lines in general formulas IV, V, VI, and VII depict the bonding pattern of cyclohexane, phenyl, or a cyclohexene that comprises exactly 1 double bond, which occurs at either A, B, or C. In some specific embodiments, the dotted lines in general formulas IV, V, VI, and VII depict the bonding pattern of cyclohexane.

In some specific embodiments, the dotted lines in general formulas IV, V, VI, and VII depict the bonding pattern of phenyl. In some specific embodiments, the dotted lines in general formulas IV, V, VI, and VII depict the bonding pattern of a cyclohexene that comprises exactly 1 double bond, which occurs at either A, B, or, in the case of formula VII, at C. In some very specific embodiments, the dotted lines in general formulas IV, V, VI, and VII depict the bonding pattern of a cyclohexene that comprises exactly 1 double bond, which occurs at A. In some very specific embodiments, the dotted lines in general formulas IV, V, VI, and VII depict the bonding pattern of a cyclohexene that comprises exactly 1 double bond, which occurs at B. In some very specific embodiments, the cannabinoid ion has the general formula VII, and the dotted lines in general formula VII depict the bonding pattern of a cyclohexene that comprises exactly 1 double bond, which occurs at C.

In some embodiments, $R_1$ is methyl; ethyl; propyl; butyl; pentyl; hexyl; heptyl; octyl; nonyl; decyl; prop-2-yl; but-2-yl; pent-2-yl; hex-2-yl; hept-2-yl; octan-2-yl; nonan-2-yl; decan-2-yl; 2-methylpropyl; 2-methylbutyl; 2-methylpentyl; 2-methylhexyl; 2-methylheptyl; 2-methyloctyl; 2-methylnonyl; 2-methyldecyl; 2-methylprop-2-yl; 2-methylbut-2-yl; 2-methylpent-2-yl; 2-methylhex-2-yl; 2-methylhept-2-yl; 2-methyloctan-2-yl; 2-methylnonan-2-yl; 2-methyldecan-2-yl; 3-methylbut-2-yl; 3-methylpent-2-yl; 3-methylhex-2-yl; 3-methylhept-2-yl; 3-methyloctan-2-yl; 3-methylnonan-2-yl; 3-methyldecan-2-yl; 2,3-dimethylbut-2-yl; 2,3-dimethylpent-2-yl; 2,3-dimethylhex-2-yl; 2,3-dimethylhept-2-yl; 2,3-dimethyloctan-2-yl; 2,3-dimethylnonan-2-yl; 2,3-dimethyldecan-2-yl; cyclopropyl; 1-methylcyclopropyl; 1-ethylcyclopropyl; 1-propylcyclopropyl; 1-butylcyclopropyl; 1-pentylcyclopropyl; 1-hexylcyclopropyl; 1-heptylcyclopropyl; 1-octylcyclopropyl; 1-nonylcyclopropyl; cyclobutyl; 1-methylcyclobutyl; 1-ethylcyclobutyl; 1-propylcyclobutyl; 1-butylcyclobutyl; 1-pentylcyclobutyl; 1-hexylcyclobutyl; 1-heptylcyclobutyl; 1-octylcyclobutyl; cyclopentyl; 1-methylcyclopentyl; 1-ethylcyclopentyl; 1-propylcyclopentyl; 1-butylcyclopentyl; 1-pentylcyclopentyl; 1-hexylcyclopentyl; 1-heptylcyclopentyl; cyclohexyl; 1-methylcyclohexyl; 1-ethylcyclohexyl; 1-propylcyclohexyl; 1-butylcyclohexyl; 1-pentylcyclohexyl; 1-hexylcyclohexyl; ethenyl; prop-1-enyl; but-1-enyl; pent-1-enyl; hex-1-enyl; hept-1-enyl; octan-1-enyl; nonan-1-enyl; decan-1-enyl; ethynyl; prop-1-ynyl; but-1-ynyl; pent-1-ynyl; hex-1-ynyl; hept-1-ynyl; octan-1-ynyl; nonan-1-ynyl; decan-1-ynyl; 2-phenylethyl; or adamantyl. In some specific embodiments, $R_1$ is propyl or pentyl. In some very specific embodiments, $R_1$ is pentyl. In some very specific embodiments, $R_1$ is propyl.

In some embodiments, $R_2$ is H.

In some embodiments, $R_3$ is H.

In some embodiments, $R_4$ is hydroxy.

In some embodiments, $R_5$ is 3-methylbut-2-enyl or 3,7-dimethylocta-2,6-dienyl. In some specific embodiments, $R_5$ is 3,7-dimethylocta-2,6-dienyl.

In some embodiments, $R_6$ is H; 2-propyl; propen-2-yl; 3-hydroxypropyl; 3-hydroxypropen-2-yl; 4-hydroxy-1-methylbutyl; 4-hydroxy-1-methylbut-2-enyl; 4-hydroxy-1-methylbut-2-ynyl; 1-fluoroethenyl; or 3-fluoropropen-2-yl. In some specific embodiments, $R_6$ is propen-2-yl (which is also referred to as isopropenyl).

In some embodiments, $R_7$ is methyl, hydroxymethyl, fluoromethyl, or oxo. In some specific embodiments, $R_7$ is methyl.

In some embodiments, $R_8$ is H.

In some embodiments, $R_9$ is H.

In some embodiments, $R_{10}$ is H; methyl; 4-methylpent-3-enyl; hydroxymethyl; 3-hydroxypropyl; 3-hydroxyprop-1-enyl; 3-hydroxyprop-1-ynyl; fluoro; or fluoromethyl. In some specific embodiments, $R_{10}$ is methyl.

In some embodiments, $R_{11}$ is methyl.

In some embodiments, $R_{12}$ is H, methoxy, ethoxy, or 2-propoxy.

In some embodiments, the cannabinoid ion has the general formula IV, V, VI, or VII; the dotted lines in general formulas IV, V, VI, and VII depict the bonding pattern of cyclohexene; and the cyclohexene comprises exactly 1 double bond, which occurs at either A or B. In some specific embodiments, the cannabinoid ion has the general formula IV, V, VI, or VII; the dotted lines in general formulas IV, V, VI, and VII depict the bonding pattern of cyclohexene; and the cyclohexene comprises exactly 1 double bond, which occurs at A.

In some embodiments, the cannabinoid ion has the general formula VII; and the dotted lines in general formula VII depict the bonding pattern of phenyl.

In some embodiments, the cannabinoid ion is either: 2-(3,7-dimethylocta-2,6-diene-1-yl)-3-alkoxy-5-alkylbenzene-1-oxide; 2-(3,7-dimethylocta-2,6-diene-1-yl)-5-alkyl-1,4-benzoquinone-3-oxide; 3-(3,7-dimethylocta-2,6-diene-1-yl)-6-alkyl-1,2-benzoquinone-4-oxide; 2-(6-isopropenyl-3-methylcyclohex-2-en-1-yl)-3-alkoxy-5-alkylbenzene-1-oxide; 2-(6-isopropenyl-3-methylcyclohex-3-en-1-yl)-3-alkoxy-5-alkylbenzene-1-oxide; 2-(6-isopropenyl-3-methylcyclohex-2-en-1-yl)-5-alkyl-1,4-benzoquinone-3-oxide; 2-(6-isopropenyl-3-methylcyclohex-3-en-1-yl)-5-alkyl-1,4-benzoquinone-3-oxide; 3-(6-isopropenyl-3-methylcyclohex-2-en-1-yl)-6-alkyl-1,2-benzoquinone-4-oxide; 3-(6-isopropenyl-3-methylcyclohex-3-en-1-yl)-6-alkyl-1,2-benzoquinone-4-oxide; 4-fluoro-2-(6-isopropenyl-3-methylcyclohex-2-en-1-yl)-3-alkoxy-5-alkylbenzene-1-oxide; 4-fluoro-2-(6-isopropenyl-3-methylcyclohex-3-en-1-yl)-3-alkoxy-5-alkylbenzene-1-oxide; 6-fluoro-2-(6-isopropenyl-3-methylcyclohex-2-en-1-yl)-5-alkyl-1,4-benzoquinone-3-oxide; 6-fluoro-2-(6-isopropenyl-3-methylcyclohex-3-en-1-yl)-5-alkyl-1,4-benzoquinone-3-oxide; 5-fluoro-3-(6-isopropenyl-3-methylcyclohex-2-en-1-yl)-6-alkyl-1,2-benzoquinone-4-oxide; 5-fluoro-3-(6-isopropenyl-3-methylcyclohex-3-en-1-yl)-6-alkyl-1,2-benzoquinone-4-oxide; 6,6,9-trimethyl-3-alkyl-6a,7,8,10a-tetrahydro-6H-benzo[c]chromen-1-oxide; 6,6,9-trimethyl-3-alkyl-6a,7,10,10a-tetrahydro-6H-benzo[c]chromen-1-oxide; 6,6,9-trimethyl-3-alkyl-7,8,9,10-tetrahydro-6H-benzo[c]chromen-1-oxide; 9-oxo-6,6-dimethyl-3-alkyl-6a,7,8,10,10a-hexahydro-9H-benzo[c]chromen-1-oxide; 6,6,9-trimethyl-3-alkyl-6H-benzo[c]chromen-1-oxide; 2-methyl-2-(4-methylpent-3-en-1-yl)-7-alkyl-2H-1-benzopyran-5-oxide; or 3-alkyl-5-oxo-6-(3,7-dimethylocta-2,6-diene-1-ylidene)-cyclohexa-1,3-diene-1-oxide. When "alkyl" is used without further context such as in the name of cannabinoid ion, then "alkyl" refers to a straight or branched $C_1$-$C_{12}$ alkyl that is optionally substituted by phenyl or a cycloalkyl. "Substituted by phenyl or a cycloalkyl" refers to the substitution of at least one hydrogen atom of a hydrocarbon chain with either phenyl or a cycloalkyl. When "alkoxy" is used without further context such as in the name of cannabinoid ion, then "alkoxy" consists of hydroxy and a straight or branched $C_1$-$C_6$ alkoxy.

In some embodiments, alkyl is methyl; ethyl; propyl; butyl; pentyl; hexyl; heptyl; octyl; nonyl; decyl; prop-2-yl; but-2-yl; pent-2-yl; hex-2-yl; hept-2-yl; octan-2-yl; nonan-2-yl; decan-2-yl; 2-methylpropyl; 2-methylbutyl; 2-methylpentyl; 2-methylhexyl; 2-methylheptyl; 2-methyloctyl;

2-methylnonyl; 2-methyldecyl; 2-methylprop-2-yl; 2-methylbut-2-yl; 2-methylpent-2-yl; 2-methylhex-2-yl; 2-methylhept-2-yl; 2-methyloctan-2-yl; 2-methylnonan-2-yl; 2-methyldecan-2-yl; 3-methylbut-2-yl; 3-methylpent-2-yl; 3-methylhex-2-yl; 3-methylhept-2-yl; 3-methyloctan-2-yl; 3-methylnonan-2-yl; 3-methyldecan-2-yl; 2,3-dimethylbut-2-yl; 2,3-dimethylpent-2-yl; 2,3-dimethylhex-2-yl; 2,3-dimethylhept-2-yl; 2,3-dimethyloctan-2-yl; 2,3-dimethylnonan-2-yl; 2,3-dimethyldecan-2-yl; cyclopropyl; 1-methylcyclopropyl; 1-ethylcyclopropyl; 1-propylcyclopropyl; 1-butylcyclopropyl; 1-pentylcyclopropyl; 1-hexylcyclopropyl; 1-heptylcyclopropyl; 1-octylcyclopropyl; 1-nonylcyclopropyl; cyclobutyl; 1-methylcyclobutyl; 1-ethylcyclobutyl; 1-propylcyclobutyl; 1-butylcyclobutyl; 1-pentylcyclobutyl; 1-hexylcyclobutyl; 1-heptylcyclobutyl; 1-octylcyclobutyl; cyclopentyl; 1-methylcyclopentyl; 1-ethylcyclopentyl; 1-propylcyclopentyl; 1-butylcyclopentyl; 1-pentylcyclopentyl; 1-hexylcyclopentyl; 1-heptylcyclopentyl; cyclohexyl; 1-methylcyclohexyl; 1-ethylcyclohexyl; 1-propylcyclohexyl; 1-butylcyclohexyl; 1-pentylcyclohexyl; 1-hexylcyclohexyl; or adamantyl. In some specific embodiments, alkyl is propyl or pentyl. In some very specific embodiments, alkyl is pentyl. In some very specific embodiments, alkyl is propyl.

In some embodiments, alkoxy is hydroxy, methoxy, ethoxy, or 2-propoxy. In some specific embodiments, alkoxy is hydroxy.

In some embodiments, the cannabinoid ion is either: 2-(3,7-dimethylocta-2,6-diene-1-yl)-3-hydroxy-5-pentylbenzene-1-oxide; 2-(3,7-dimethylocta-2,6-diene-1-yl)-5-pentyl-1,4-benzoquinone-3-oxide; 3-(3,7-dimethylocta-2,6-diene-1-yl)-6-pentyl-1,2-benzoquinone-4-oxide; 2-(6-isopropenyl-3-methylcyclohex-2-en-1-yl)-3-hydroxy-5-pentylbenzene-1-oxide; 2-(6-isopropenyl-3-methylcyclohex-3-en-1-yl)-3-hydroxy-5-pentylbenzene-1-oxide; 2-(6-isopropenyl-3-methylcyclohex-2-en-1-yl)-5-pentyl-1,4-benzoquinone-3-oxide; 2-(6-isopropenyl-3methylcyclohex-3-en-1-yl)-5-pentyl-1,4-benzoquinone-3-oxide; 3-(6-isopropenyl-3-methylcyclohex-2-en-1-yl)-6-pentyl-1,2-benzoquinone-4-oxide; 3-(6-isopropenyl-3-methylcyclohex-3-en-1-yl)-6-pentyl-1,2-benzoquinone-4-oxide; 4-fluoro-2-(6-isopropenyl-3-methylcyclohex-2-en-1-yl)-3-hydroxy-5-pentylbenzene-1-oxide; 4-fluoro-2-(6-isopropenyl-3-methylcyclohex-3-en-1-yl)-3-hydroxy-5-pentylbenzene-1-oxide; 6-fluoro-2-(6-isopropenyl-3-methylcyclohex-2-en-1-yl)-5-pentyl-1,4-benzoquinone-3-oxide; 6-fluoro-2-(6-isopropenyl-3-methylcyclohex-3-en-1-yl)-5-pentyl-1,4-benzoquinone-3-oxide; 5-fluoro-3-(6-isopropenyl-3-methylcyclohex-2-en-1-yl)-6-pentyl-1,2-benzoquinone-4-oxide; 5-fluoro-3-(6-isopropenyl-3-methylcyclohex-3-en-1-yl)-6-pentyl-1,2-benzoquinone-4-oxide; 6,6,9-trimethyl-3-pentyl-6a,7,8,10a-tetrahydro-6H-benzo[c]chromen-1-oxide; 6,6,9-trimethyl-3-pentyl-6a,7,10,10a-tetrahydro-6H-benzo[c]chromen-1-oxide; 6,6,9-trimethyl-3-pentyl-6H-benzo[c]chromen-1-oxide; 2-methyl-2-(4-methylpent-3-en-1-yl)-7-pentyl-2H-1-benzopyran-5-oxide; 3-pentyl-5-oxo-6-(3,7-dimethylocta-2,6-diene-1-ylidene)-cyclohexa-1,3-diene-1-oxide; 2-(3,7-dimethylocta-2,6-diene-1-yl)-3-hydroxy-5-propylbenzene-1-oxide; 2-(3,7-dimethylocta-2,6-diene-1-yl)-5-propyl-1,4-benzoquinone-3-oxide; 3-(3,7-dimethylocta-2,6-diene-1-yl)-6-propyl-1,2-benzoquinone-4-oxide; 2-(6-isopropenyl-3-methylcyclohex-2-en-1-yl)-3-hydroxy-5-propylbenzene-1-oxide; 2-(6-isopropenyl-3-methylcyclohex-3-en-1-yl)-3-hydroxy-5-propylbenzene-1-oxide; 2-(6-isopropenyl-3-methylcyclohex-2-en-1-yl)-5-propyl-1,4-benzoquinone-3-oxide; 2-(6-isopropenyl-3-methylcyclohex-3-en-1-yl)-5-propyl-1,4-benzoquinone-3-oxide; 3-(6-isopropenyl-3-methylcyclohex-2-en-1-yl)-6-propyl-1,2-benzoquinone-4-oxide; 3-(6-isopropenyl-3-methylcyclohex-3-en-1-yl)-6-propyl-1,2-benzoquinone-4-oxide; 6,6,9-trimethyl-3-propyl-6a,7,8,10a-tetrahydro-6H-benzo[c]chromen-1-oxide; 6,6,9-trimethyl-3-propyl-6a,7,10,10a-tetrahydro-6H-benzo[c]chromen-1-oxide; 6,6,9-trimethyl-3-propyl-6H-benzo[c]chromen-1-oxide; 2-methyl-2-(4-methylpent-3-en-1-yl)-7-propyl-2H-1-benzopyran-5-oxide; 3-propyl-5-oxo-6-(3,7-dimethylocta-2,6-diene-1-ylidene)-cyclohexa-1,3-diene-1-oxide; or 9-oxo-6,6-dimethyl-3-(2-methyloctan-2-yl)-6,6a,7,8,10,10a-hexahydro-9H-benzo[c]chromen-1-oxide.

In some embodiments, the composition is formulated for oral administration to a human or an animal. In some embodiments, the composition is formulated for topical administration to a human or an animal.

Various aspects of this patent document relate to a medicament, comprising a composition disclosed anywhere in this patent document.

Various aspects of this patent document relate to a method to administer a composition to a subject, comprising orally administering a composition disclosed anywhere in this patent document to the subject, wherein the subject is a human or an animal.

Various aspects of this patent document relate to a method to administer a composition to a subject, comprising topically administering a composition disclosed anywhere in this patent document to the subject, wherein the subject is a human or an animal.

In some embodiments, the animal is a rodent, lagomorph, feline, canine, porcine, ovine, lama, vicugna, bovine, equine, or primate.

Exemplification. Examples 1-7 set forth specific embodiments of this disclosure, and examples 1-7 do not limit the scope of the disclosure or any claim that matures from this patent document.

Example 1. Formulation of the Cannabidiol Anion Dissolved in Glycerol

Cannabidiol is deprotonated in 0.5 molar potassium hydroxide in 190 proof ethanol to produce cannabidiol anion (2-(6-isopropenyl-3-methylcyclohex-2-en-1-yl)-3-hydroxy-5-pentylbenzene-1-oxide). The cannabidiol anion in 190 proof ethanol is combined with glycerol to produce a formulation comprising approximately 25 percent ethanol by volume and 25 grams cannabidiol anion per liter, which is greater than the solubility of molecular cannabidiol in 25:75 by volume ethanol:glycerol.

Example 2. The Cannabidiol Anion Displays Efficacy at Arresting Active Seizures in Canine The FDA- and EMA-approved cannabidiol pharmaceutical EPIDIOLEX® is administered at 5-20 mg/kg/day to treat epilepsy, but EPIDIOLEX® is not known to arrest active seizures. A single oral dose of 0.5-1.0 mg/kg cannabidiol anion in a formulation prepared according to Example 1 both consistently and instantaneously arrested active seizures in an epileptic Entlebucher Mountain Dog resulting in reduced seizure duration and severity. Cytochrome P450 metabolizes a significant portion of EPIDIOLEX®. The rapid onset of the cannabidiol anion formulated in glycerol suggests that at least a portion avoided first-pass metabolism.

Example 3. Formulation of the Cannabigerol Anion Dissolved in Glycerol

Cannabigerol is deprotonated in 0.5 molar potassium hydroxide in 190 proof ethanol to produce cannabigerol anion (2-(3,7-dimethylocta-2,6-diene-1-yl)-3-hydroxy-5-pentylbenzene-1-oxide). The cannabigerol anion in 190 proof ethanol is combined with glycerol to produce a formulation comprising approximately 25 percent ethanol by volume and 25 grams cannabigerol anion per liter.

Example 4. The Cannabigerol Anion Displays Efficacy Against Insomnia in Humans An adult human who presented with chronic insomnia consumed approximately 25 milligrams of cannabigerol anion in a formulation prepared according to Example 3. The individual reported a sedative effect that was effective at treating the insomnia with an onset time of less than five minutes. The rapid onset of the cannabigerol anion formulated in glycerol suggests that at least a portion avoided first-pass metabolism.

Example 5. Formulation of the Tetrahydrocannabinol Anion Dissolved in Glycerol Tetrahydrocannabinol is deprotonated in 0.5 molar potassium hydroxide in 190 proof ethanol to produce tetrahydrocannabinol anion (6,6,9-trimethyl-3-pentyl-6a,7,8,10a-tetrahydro-6H-benzo[c]chromen-1-oxide). The tetrahydrocannabinol anion in 190 proof ethanol is combined with glycerol to produce a formulation comprising approximately 25 percent ethanol by volume and 1 gram tetrahydrocannabinol anion per liter.

Example 6. Ionizing Tetrahydrocannabinol Attenuates its Psychoactive Effects The psychoactive effects of tetrahydrocannabinol largely stem from its cytochrome P450 oxidation product 11-hydroxy-tetrahydrocannabinol. A standard oral dose of recreational tetrahydrocannabinol is 10 milligrams. An adult human orally consumed 10 milligrams of tetrahydrocannabinol anion in a formulation prepared according to Example 5. The individual reported no marked psychoactive effect, which suggests that the tetrahydrocannabinol anion may have avoided conversion into 11-hydroxy-tetrahydrocannabinol by avoiding first-pass metabolism.

Example 7. Formulation of the Cannabidivarin Anion, Cannabichromene Anion, and Cannabinol Anion Dissolved in Glycerol Distilled industrial hemp extract containing 79 percent cannabidiol, 4 percent cannabichromene, 1.6 percent tetrahydrocannabinol, 0.5 percent cannabidivarin, and 0.4 percent cannabinol was incubated in 0.5 molar potassium hydroxide in 190 proof ethanol to produce cannabidiol anion, cannabichromene anion (2-methyl-2-(4-methylpent-3-en-1-yl)-7-propyl-2H-1-benzopyran-5-oxide), tetrahydrocannabinol anion, cannabidivarin anion (2-(6-isopropenyl-3-methylcyclohex-2-en-1-yl)-3-hydroxy-5-propylbenzene-1-oxide), and cannabinol anion (6,6,9-trimethyl-3-pentyl-6H-benzo[c]chromen-1-oxide). The anions and ethanol were combined with glycerol to produce a formulation comprising approximately 25 percent ethanol by volume, 25 grams cannabidiol anion per liter, 1.3 grams cannabichromene anion per liter, 0.5 grams tetrahydrocannabinol anion per liter, 0.2 grams cannabidivarin anion per liter, and 0.1 grams cannabinol anion per liter. The formulation was administered to humans as a tincture.

What is claimed is:

1. A composition, comprising a liquid phase that comprises a solute and a solvent, wherein the solute is a cannabinoid ion; the cannabinoid ion is 3-(3,7-dimethylocta-2,6-diene-1-yl)-6-pentyl-1,2-benzoquinone-4-oxide; the solvent is glycerol; and the cannabinoid ion is dissolved in the glycerol.

2. The composition of claim 1, comprising the glycerol at a concentration of at least 50 percent by weight.

3. The composition of claim 1, comprising ethanol.

4. The composition of claim 1, comprising water.

5. The composition of claim 1, comprising a metal cation.

6. The composition of claim 5, wherein the metal cation is sodium cation ("Na+").

7. The composition of claim 5, wherein the metal cation is potassium cation ("K+").

8. The composition of claim 5, comprising the metal cation and the cannabinoid ion at a molar ratio of at least 1:1 and no greater than 5:4.

9. The composition of claim 1, comprising a concentration of the cannabinoid ion that is dissolved in the glycerol, wherein the cannabinoid ion has a conjugate acid that has a solubility in the liquid phase that is less than the concentration of the cannabinoid ion that is dissolved in the glycerol.

10. The composition of claim 1, comprising a molecule and the cannabinoid ion at a molar ratio of at least 1:1,000,000 and less than 1:1, wherein the cannabinoid ion has a conjugate acid; and the molecule is the conjugate acid of the cannabinoid ion.

11. The composition of claim 1, comprising the cannabinoid ion at a concentration of at least 1 gram per liter.

12. The composition of claim 1, wherein the composition is formulated for oral administration to a human or an animal.

13. The composition of claim 1, wherein the composition is formulated for topical administration to a human or an animal.

14. A medicament, comprising a composition according to claim 1.

15. A method to administer a composition to a subject, comprising orally administering a composition according to claim 1 to the subject, wherein the subject is a human or an animal.

16. A method to administer a composition to a subject, comprising topically administering a composition according to claim 1 to the subject, wherein the subject is a human or an animal.

17. A composition, comprising a liquid phase that comprises a solute and a solvent, wherein the solute is a cannabinoid ion; the cannabinoid ion is 2-(3,7-dimethylocta-2,6-diene-1-yl)-3-hydroxy-5-pentylbenzene-1-oxide; the solvent is glycerol; and the cannabinoid ion is dissolved in the glycerol.

18. A method to administer a composition to a subject, comprising topically administering a composition according to claim 17 to the subject, wherein the subject is a human.

19. A composition, comprising a liquid phase that comprises a solute and a solvent, wherein the solute is a cannabinoid ion; the cannabinoid ion is 2-(3,7-dimethylocta-2,6-diene-1-yl)-5-pentyl-1,4-benzoquinone-3-oxide; the solvent is glycerol; and the cannabinoid ion is dissolved in the glycerol.

20. A method to administer a composition to a subject, comprising topically administering a composition according to claim 19 to the subject, wherein the subject is a human.

\* \* \* \* \*